United States Patent

Iwata et al.

[11] Patent Number: 4,749,704
[45] Date of Patent: Jun. 7, 1988

[54] CYCLOPENTA[D]PYRIMIDINE DERIVATIVES AND USE AS ANTIDEPRESSANTS

[75] Inventors: Nobuyoshi Iwata; Isao Nakayama; Kanichi Nakamura, all of Hiromachi; Tomio Kimura; Takashi Kobayashi, both of Ube, all of Japan

[73] Assignees: Sankyo Company Limited, Tokyo; Ube Industries Limited, Ube, both of Japan

[21] Appl. No.: 837,079

[22] Filed: Mar. 6, 1986

[30] Foreign Application Priority Data

Mar. 7, 1985 [JP] Japan ............................ 60-43626

[51] Int. Cl.⁴ .................. A61K 31/505; C07D 239/70
[52] U.S. Cl. ............................................. 514/258; 544/253
[58] Field of Search ........................ 544/253; 514/258

[56] References Cited

U.S. PATENT DOCUMENTS 3,915,976 10/1975 Salmond ............................ 544/253
3,980,650 9/1976 Nauta ............................... 544/253 X
4,435,402 3/1984 Tsuji et al. ........................ 514/258 X
4,450,162 5/1984 Kamioka et al. ................. 544/253 X Primary Examiner—Donald G. Daus
Assistant Examiner—Diana G. Rivers
Attorney, Agent, or Firm—Frishauf, Holtz, Goodman & Woodward

[57] ABSTRACT

Compounds of formula (I):

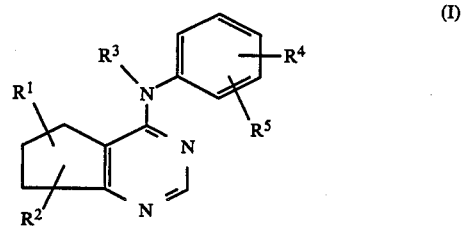

(wherein $R^1$ and $R^2$ are hydroxy, alkoxy, aryloxy or acyloxy or $R^2$ is hydrogen, $R^3$ is hydrogen or alkyl and $R^4$ and $R^5$ are hydrogen or various organic substituents) have valuable antidepressant activity and may be used in the treatment of mental depression.

27 Claims, No Drawings

CYCLOPENTA[D]PYRIMIDINE DERIVATIVES AND USE AS ANTIDEPRESSANTS

BACKGROUND TO THE INVENTION

The present invention relates to a series of new anilino-substituted cyclopenta[d]pyrimidine derivatives having valuable antidepressant activity, to a process for preparing these compounds and to a pharmaceutical composition containing them.

A variety of compounds having antidepressant activity is known and many of these are used in the treatment of mental depression. The compounds mainly used for this purpose are commonly classified into two groups: the "monoamine oxidase inhibitors", which are mostly hydrazine derivatives; and the "tricyclic antidepressants", which mainly have a dibenzazepine or dibenzocycloheptene structure ["Martindale: The Extra Pharmacopoeia", twenty-seventh Edition (1977), published by the Pharmaceutical Press, London]. Of these classes, the tricyclic antidepressants are generally considered to be more effective than the monoamine oxidase inhibitors and are therefore preferred; one of the most preferred of the tricyclic antidepressants in current use is imipramine. All of the currently available antidepressants exhibit a variety of side-effects of varying degrees of seriousness, which result in their use being somewhat restricted. Imipramine, for example, exhibits antihistaminic and anticholinergic activities.

The known classes of antidepressant, however, have a totally different molecular structure from the compounds of the invention.

A class of antidepressant pyrimidine derivatives, including some related to the compounds of the invention, is disclosed in U.S. Pat. No. 4,450,162. The majority of the compounds disclosed in that U.S. Pat. are simple pyrimidine derivatives. However, included amongst them are some cyclopenta[d]pyrimidine derivatives which differ from those of the present invention in having hydrogen atoms at all of the 5, 6 and 7 positions of the cyclopenta[d]pyrimidine nucleus, whereas the compounds of the present invention have hydroxy or substituted hydroxy groups at one or two of these positions.

It is believed that at least one of the compounds of the invention—that of formula (I) given below, where $R^1$=OH, $R^2$=H, $R^3$=H, $R^4$=4-CN and $R^5$=H—may be a product of the canine metabolism of the corresponding prior art compound corresponding to formula (I) given below but where $R^1$=H, as the compound of the invention has been isolated by us from the urine of a dog to which the prior art compound had been orally administered.

BRIEF SUMMARY OF INVENTION

It is, therefore, an object of the present invention to provide a series of new cyclopenta[d]pyrimidine derivatives having antidepressant activity.

It is a further, and more specific, object of the invention to provide such compounds having reduced toxicity and side-effects.

The compounds of the invention are those cyclopenta[d]pyrimidine derivatives having the formula (I):

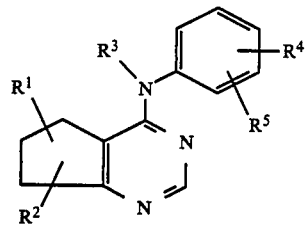

wherein:

$R^1$ represents a hydroxy group, a $C_1$-$C_4$ alkoxy group, a substituted $C_1$-$C_4$ alkoxy group having at least one substituent selected from the group consisting of substituents (a), a $C_2$-$C_4$ alkenyloxy group, an aryloxy group, a $C_2$-$C_5$ aliphatic acyloxy group, a substituted $C_2$-$C_5$ aliphatic acyloxy group having at least one substituent selected from the group consisting of substituents (a) or an aromatic acyloxy group;

$R^2$ represents a hydrogen atom, a hydroxy group, a $C_1$-$C_4$ alkoxy group, a substituted $C_1$-$C_4$ alkoxy group having at least one substituent selected from the group consisting of substituents (a), a $C_2$-$C_4$ alkenyloxy group, an aryloxy group, a $C_2$-$C_5$ aliphatic acyloxy group, a substituted $C_2$-$C_5$ aliphatic acyloxy group having at least one substituent selected from the group consisting of substituents (a) or an aromatic acyloxy group;

$R^3$ represents a hydrogen atom or a $C_1$-$C_4$ alkyl group;

$R^4$ and $R^5$ are independently selected from the group consisting of hydrogen atoms, $C_1$-$C_4$ alkyl groups, $C_1$-$C_4$ alkoxy groups, hydroxy groups, $C_2$-$C_5$ aliphatic acyloxy groups, aryloxy groups, $C_1$-$C_4$ haloalkyl groups, halogen atoms, nitro groups, $C_1$-$C_4$ alkanesulfonyl groups, arylsulfonyl groups, cyano groups and carboxy groups; or $R^4$ and $R^5$ together represent a $C_1$ or $C_2$ alkylenedioxy group;

said substituents (a) are selected from the group consisting of $C_1$-$C_4$ alkoxy groups, $C_3$-$C_7$ cycloalkyl groups, halogen atoms, dialkylamino groups where both alkyl parts are $C_1$-$C_4$, aromatic acyl groups and aryl groups;

said aryl groups and the aryl parts of said aromatic acyl, aromatic acyloxy, aryloxy and arylsulfonyl groups being $C_6$-$C_{10}$ carbocyclic aromatic hydrocarbon groups which are unsubstituted or have at least one substituent selected from the group consisting of substituents (b); and said substituents (b) are selected from the group consisting of $C_1$-$C_4$ alkyl groups, $C_1$-$C_4$ alkoxy groups, $C_3$-$C_7$ cycloalkyl groups, halogen atoms and dialkylamino groups where both alkyl parts are $C_1$-$C_4$;

and pharmaceutically acceptable salts and esters thereof.

The invention also provides processes for preparing the compounds of the invention, these processes being as described in more detail hereafter.

The invention further provides a pharmaceutical composition for the treatment of depression, comprising an anti-depressant agent in admixture with a pharmaceutically acceptable carrier or diluent, wherein the anti-depressant agent is selected from the group consisting of compounds of formula (I) and pharmaceutically acceptable salts and esters thereof.

The invention still further provides a method of treating depressive conditions in an animal by administering to said animal an antidepressant compound, wherein said antidepressant compound is at least one compound selected from the group consisting of compounds of formula (I) and pharmaceutically acceptable salts and esters thereof.

DETAILED DESCRIPTION OF INVENTION

In the compounds of the invention, where $R^1$, $R^2$, $R^4$ or $R^5$ represents a $C_1$-$C_4$ alkoxy group, this may be a straight or branched chain group and examples include the methoxy, ethoxy, propoxy, isopropoxy, butoxy and isobutoxy groups.

Where $R^1$ or $R^2$ represents a $C_2$-$C_4$ alkenyloxy group, this may be a straight or branched chain group and examples include the vinyloxy, allyloxy and 2-butenyloxy groups, of which the allyloxy and 2-butenyloxy groups are preferred.

Where $R^1$, $R^2$, $R^4$ or $R^5$ represents an aryloxy group, the aryl part is a $C_6$-$C_{10}$ carbocyclic aromatic hydrocarbon group, preferably a phenyl or 1- or 2-naphthyl group, and this group may be substituted or unsubstituted and, if substituted, has at least one of the substituents defined above as substituents (b).

$R^1$, $R^2$, $R^4$ and $R^5$ may represent $C_2$-$C_5$ aliphatic acyloxy groups, which may be straight or branched chain groups and, in the case of the groups represented by $R^1$ and $R^2$ they may be unsubstituted or may have one or more substituents selected from the group consisting of substituents (a) defined above. The groups represented by $R^4$ and $R^5$ are unsubstituted. The acyl group may be saturated or unsaturated (these terms referring to the carbon-carbon bonds in the acyl group) and is preferably a $C_2$-$C_5$ alkanoyl or $C_3$-$C_5$ alkenoyl group. Specific examples of the unsubstituted groups which may be represented by $R^1$, $R^2$, $R^4$ and $R^5$ include the acetoxy, propionyloxy, butyryloxy, isobutyryloxy and acryloyloxy groups, of which the acetoxy group is preferred.

Where $R^1$ or $R^2$ represents an aromatic acyloxy group, the aryl part is as defined above and may be unsubstituted or may have one or more substituents selected from the group consisting of substituents (b). Examples of such substituents (b) are given below. Preferred aromatic acyloxy groups are the benzoyloxy, 1-naphthoyloxy and 2-naphthoyloxy groups, which may be substituted or unsubstituted, and an example of a preferred substituted aromatic acyloxy group is the 3,4-dimethoxybenzoyloxy group.

Where $R^3$, $R^4$ or $R^5$ represents a $C_1$-$C_4$ alkyl group, this may be a straight or branched chain alkyl group and examples include the methyl, ethyl, propyl, isopropyl, butyl and isobutyl groups. Of the alkyl groups, the $C_1$-$C_3$ alkyl groups are preferred and particularly the methyl group for $R^3$ and the ethyl group for $R^4$ and $R^5$.

Where $R^4$ or $R^5$ represents a $C_1$-$C_4$ haloalkyl group, the alkyl part may be any one of the alkyl groups exemplified above in relation to $R^3$, $R^4$ and $R^5$ and the halogen atom may be, for example, a fluorine, chlorine, bromine or iodine atom, more preferably a fluorine or chlorine atom. The alkyl group may have one or more halogen atoms, up to complete perhalogenation. Examples of such groups include the chloromethyl, dichloromethyl, iodomethyl, bromomethyl, fluoromethyl, trifluoromethyl, 2-chloroethyl, 2-bromoethyl, 2-iodoethyl, 2-fluoroethyl, 1,2-dibromoethyl, 1,2-dichloroethyl, 2,2-dichloroethyl, 2,2-difluoroethyl, 2,2,2-trichloroethyl, 2,2,2-trifluoroethyl, 2,2,2-tribromoethyl, 1,2,2-trichloroethyl, 3-chloropropyl and 1,2,3-trichloropropyl groups, of which the trifluoromethyl group is preferred.

Where $R^4$ or $R^5$ represents a halogen atom, this may be a fluorine, chlorine, bromine or iodine atom, of which the chlorine atom is preferred.

Where $R^4$ or $R^5$ represents a $C_1$-$C_4$ alkanesulfonyl group, the alkyl part may be as exemplified above in relation to the alkyl groups which may be represented by $R^3$, $R^4$ and $R^5$ and examples include the methanesulfonyl, ethanesulfonyl, propanesulfonyl and butanesulfonyl groups.

Where $R^4$ or $R^5$ represents an arylsulfonyl group, the aryl part is as defined above and may be substituted or unsubstituted. Examples of such arylsulfonyl groups include the benzenesulfonyl, p-toluenesulfonyl and naphthalenesulfonyl groups.

Where $R^4$ and $R^5$ together represent an alkylenedioxy group, this may be a methylenedioxy or ethylenedioxy group.

Where $R^4$ or $R^5$ represents a carboxy group, the resulting compounds can form esters. The nature of such esters is not critical to the invention, provided that, where the esters are to be used for therapeutic purposes, they are pharmaceutically acceptable, which, as is well-known in the art, means that the resulting esters should not have increased toxicity (or unacceptably increased toxicity) or reduced activity (or unacceptably reduced activity) as compared with the free acids. Preferred esters are the $C_1$-$C_4$ alkyl esters, for example the methyl, ethyl, propyl, isopropyl, butyl, isobutyl, sec-butyl and t-butyl esters, of which the methyl, ethyl, propyl and isopropyl esters are preferred.

Where $R^1$ or $R^2$ represents a substituted $C_1$-$C_4$ alkoxy group or a substituted $C_2$-$C_5$ aliphatic acyloxy group, the substituents are chosen from substituents (a) defined above, for example:

$C_1$-$C_4$ alkoxy groups, for example those alkoxy groups exemplified above in relation to $R^1$ and $R^2$ themselves, and preferred substituted alkoxy and aliphatic acyloxy groups having such substituents include the 2-methoxyethoxy, 2-ethoxyethoxy and methoxyacetoxy groups;

$C_3$-$C_7$ cycloalkyl groups, for example the cyclopropyl, cyclobutyl, cyclopentyl, cyclohexyl and cycloheptyl groups, and a preferred substituted alkoxy group is the cyclopropylmethoxy group;

halogen atoms, for example fluorine, chlorine, bromine or iodine atoms, and preferred substituted alkoxy and aliphatic acyloxy groups include the trifluoromethoxy, chloroacetoxy and trifluoroacetoxy groups;

dialkylamino groups where each alkyl part is a $C_1$-$C_4$ alkyl group (e.g. as exemplified above in relation to the alkyl groups which may be represented by $R^3$, $R^4$ and $R^5$), for example the dimethylamino, diethylamino, dipropylamino, diisopropylamino, dibutylamino, methylethylamino and ethylpropylamino groups and preferred alkoxy and aliphatic acyloxy groups having such a substituent include the 2-dimethylaminoethoxy, 2-diethylaminoethoxy and dimethylaminoacetoxy groups;

aromatic acyl groups, for example the aromatic acyl groups corresponding to the aromatic acyloxy groups exemplified above in relation to $R^1$ and $R^2$ and an example of a preferred such substituted alkoxy group is the phenacyloxy group; and aryl groups, as defined above, for example the phenyl or naphthyl groups, which may be substituted or unsubstituted, and examples of alkoxy and aliphatic acyloxy groups containing such a substituent include the benzyloxy, 4-fluorobenzyloxy, phenylacetoxy and cinnamoyloxy groups.

Where any of the aryl groups defined above are substituted, the substituents are selected from the group consisting of substituents (b), i.e. $C_1$-$C_4$ alkyl groups (e.g. as exemplified above in relation to $R^3$, $R^4$ and $R^5$), $C_1$-$C_4$ alkoxy groups (e.g. as exemplified above in relation to $R^1$, $R^2$, $R^4$ and $R^5$), $C_3$-$C_7$ cycloalkyl groups [e.g. as exemplified above in relation to substituents (a)], halogen atoms [e.g. as exemplified above in relation to substituents (a)] and dialkylamino groups [e.g. as exemplified above in relation to substituents (a)].

A preferred class of compounds of the present invention are those compounds of formula (I) in which $R^1$ is as defined above and is at the 5- or 7-position, and $R^2$ represents a hydrogen atom; or $R^1$ and $R^2$ are the same or different and selected from those groups defined above (provided that $R^2$ is not a hydrogen atom), and one of $R^1$ and $R^2$ is at the 5-position and the other is at the 7-position.

A more preferred class of compounds of the invention are those compounds in which:

$R^1$ represents a hydroxy group, a $C_1$-$C_4$ alkoxy group or a $C_2$-$C_5$ aliphatic acyloxy group at the 5- or 7-position;

$R^2$ represents a hydrogen atom, or a hydroxy, $C_1$-$C_4$ alkoxy or $C_2$-$C_5$ aliphatic acyloxy group at the 7- or 5-position;

$R^3$ represents a hydrogen atom;

$R^4$ represents a hydrogen atom, a $C_1$-$C_4$ alkyl group, a $C_1$-$C_4$ haloalkyl group, a halogen atom, a nitro group, a $C_1$-$C_4$ alkanesulfonyl group, a cyano group, a carboxy group or a $C_2$-$C_5$ alkoxycarbonyl group; and $R^5$ represents a hydrogen or halogen atom.

A still more preferred class of compounds of the invention are those compounds in which:

$R^1$ represents a hydroxy group or an acetoxy group at the 5- or 7-position;

$R^2$ and $R^3$ both represent hydrogen atoms;

$R^4$ represents a $C_1$-$C_4$ alkyl group, a trifluoromethyl group, a halogen atom or a cyano group at the 4-position; and $R^5$ represents a hydrogen atom or a halogen atom at the 3-position.

The most preferred class of compounds of the present invention are those compounds in which:

$R^1$ represents a hydroxy group or an acetoxy group at the 5- or 7-position;

$R^2$, $R^3$ and $R^5$ all represent hydrogen atoms; and $R^4$ represents an ethyl group, a chlorine atom or a cyano group at the 4-position.

The compounds of the invention always contain at least one asymmetric carbon atom—the carbon atom to which the group represented by $R^1$ is attached—and may, where $R^2$ represents a group other than hydrogen, contain a second asymmetric carbon atom at that position also. Other asymmetric carbon atoms may be present in the compounds, depending upon the natures of the substituents $R^1$-$R^5$. Accordingly, the compounds of the invention can exist in the form of various optical isomers, and the present invention envisages both the individual, isolated isomers, as well as mixtures (which may be racemates) thereof. The compounds of the invention may be prepared in the form of individual isomers by employing individual isomers as the starting materials and/or by employing stereospecific synthesis techniques. Alternatively, where the compounds are obtained in the form of mixtures of isomers, they may be employed as such mixtures or they may be separated into the respective isomers by conventional optical resolution techniques.

The compounds of the invention contain a basic nitrogen atom and thus can form acid addition salts. The nature of such salts is not critical to the invention, provided that, where the salt is to be employed for therapeutic purposes, the salt should be pharmaceutically acceptable. Where, however, the salt is to be employed for other purposes, e.g. as an intermediate, even this restriction does not apply. Examples of acids with which the compounds of the invention may form pharmaceutically acceptable salts include, for example: mineral acids, such as hydrochloric acid, hydrobromic acid, hydroiodic acid or sulfuric acid; organic sulfonic acids, such as methanesulfonic acid, ethanesulfonic acid, benzenesulfonic acid or p-toluenesulfonic acid; and organic carboxylic acids, such as oxalic acid, maleic acid, fumaric acid, tartaric acid or citric acid.

Examples of the compounds of the invention are given in the following list. Where appropriate, these compounds are hereafter identified by the numbers appended to them in this list.

1. 4-Anilino-6,7-dihydro-7-hydroxy-5H-cyclopenta[d]pyrimidine
2. 4-Anilino-6,7-dihydro-5-hydroxy-5H-hydroxy-5H-cyclopenta[d]pyrimidine
3. 4-(4-Ethylanilino)-6,7-dihydro-7-hydroxy-5H-cyclopenta[d]pyrimidine
4. 4-(4-Ethylanilino)-6,7-dihydro-5-hydroxy-5H-cycloopenta[d]pyrimidine
5. 6,7-Dihydro-7-hydroxy-4-(4-isopropylanilino)-5H-cyclopenta[d]pyrimidine
6. 6,7-Dihydro-5-hydroxy-4-(4-isopropylanilino)-5H-cyclopenta[d]pyrimidine
7. 6,7-Dihydro-7-hydroxy-4-(3-methoxyanilino)-5H-cyclopenta[d]pyrimidine
8. 6,7-Dihydro-5-hydroxy-4-(3-methoxyanilino)-5H-cyclopenta[d]pyrimidine
9. 6,7-Dihydro-7-hydroxy-4-(4-methoxyanilino)-5H-cyclopenta[d]pyrimidine
10. 6,7-Dihydro-5-hydroxy-4-(4-methoxyanilino)-5H-cyclopenta[d]pyrimidine
11. 4-(3-Ethoxyanilino)-6,7-dihydro-7-hydroxy-5H-cyclopenta[d]pyrimidine
12. 4-(3-Ethoxyanilino)-6,7-dihydro-5-hydroxy-5H-cyclopenta[d]pyrimidine
13. 4-(4-Ethoxyanilino)-6,7-dihydro-7-hydroxy-5H-cyclopenta[d]pyrimidine
14. 4-(4-Ethoxyanilino)-6,7-dihydro-5-hydroxy-5H-cyclopenta[d]pyrimidine
15. 4-(2,4-Dimethoxyanilino)-6,7-dihydro-7-hydroxy-5H-cyclopenta[d]pyrimidine
16. 4-(2,4-Dimethoxyanilino)-6,7-dihydro-5-hydroxy-5H-cyclopenta[d]pyrimidine
17. 6,7-Dihydro-7-hydroxy-4-(3,4-methylenedioxyanilino)-5H-cyclopenta[d]pyrimidine
18. 6,7-Dihydro-5-hydroxy-4-(3,4-methylenedioxyanilino)-5H-cyclopenta[d]pyrimidine
19. 4-(3-Chloroanilino)-6,7-dihydro-7-hydroxy-5H-cyclopenta[d]pyrimidine
20. 4-(3-Chloroanilino)-6,7-dihydro-5-hydroxy-5H-cyclopenta[d]pyrimidine
21. 4-(4-Chloroanilino)-6,7-dihydro-7-hydroxy-5H-cyclopenta[d]pyrimidine
22. 4-(4-Chloroanilino)-6,7-dihydro-5-hydroxy-5H-cyclopenta[d]pyrimidine 23. 4-(4-Bromoanilino)-6,7-dihydro-7-hydroxy-5H-cyclopenta[d]pyrimidine
24. 4-(4-Bromoanilino)-6,7-dihydro-5-hydroxy-5H-cyclopenta[d]pyrimidine
25. 4-(4-Fluoroanilino)-6,7-dihydro-7-hydroxy-5H-cyclopenta[d]pyrimidine
26. 4-(4-Fluoroanilino)-6,7-dihydro-5-hydroxy-5H-cyclopenta[d]pyrimidine
27. 6,7-Dihydro-7-hydroxy-4-(4-iodoanilino)-5H-cyclopenta[d]pyrimidine
28. 6,7-Dihydro-5-hydroxy-4-(4-iodoanilino)-5H-cyclopenta[d]pyrimidine
29. 6,7-Dihydro-7-hydroxy-4-(4-trifluoromethylanilino)-5H-cyclopenta[d]pyrimidine
30. 6,7-Dihydro-5-hydroxy-4-(4-trifluoromethylanilino)-5H-cyclopenta[d]pyrimidine
31. 4-(4-Cyanoanilino)-6,7-dihydro-7-hydroxy-5H-cyclopenta[d]pyrimidine
32. 4-(4-Cyanoanilino)-6,7-dihydro-5-hydroxy-5H-cyclopenta[d]pyrimidine
33. 6,7-Dihydro-7-hydroxy-4-(4-nitroanilino)-5H-cyclopenta[d]pyrimidine
34. 6,7-Dihydro-5-hydroxy-4-(4-nitroanilino)-5H-cyclopenta[d]pyrimidine
35. 6,7-Dihydro-7-hydroxy-4-(4-hydroxyanilino)-5Hcyclopenta[d]pyrimidine
36. 6,7-Dihydro-5-hydroxy-4-(4-hydroxyanilino)-5H-cyclopenta[d]pyrimidine
37. 4-(3,4-Dichloroanilino)-6,7-dihydro-7-hydroxy-5H-cyclopenta[d]pyrimidine
38. 4-(3,4-Dichloroanilino)-6,7-dihydro-5-hydroxy-5H-cyclopenta[d]pyrimidine
39. 4-(4-Chloro-3-trifluoromethylanilino)-6,7-dihydro-7-hydroxy-5H-cyclopenta[d]pyrimidine
40. 4-(4-Chloro-3-trifluoromethylanilino)-6,7-dihydro-5-hydroxy-5H-cyclopenta[d]pyrimidine
41. 6,7-Dihydro-7-hydroxy-4-(4-methanesulfonylanilino)-5H-cyclopenta[d]pyrimidine
42. 6,7-Dihydro-5-hydroxy-4-(4-methanesulfonylanilino)-5H-cyclopenta[d]pyrimidine
43. 4-(4-Carboxyanilino)-6,7-dihydro-7-hydroxy-5H-cyclopenta[d]pyrimidine
44. 4-(4-Carboxyanilino)-6,7-dihydro-5-hydroxy-5H-cyclopenta[d]pyrimidine
45. 6,7-Dihydro-7-hydroxy-4-(4-methoxycarbonylanilino)-5H-cyclopenta[d]pyrimidine
46. 6,7-Dihydro-5-hydroxy-4-(4-methoxycarbonylanilino)-5H-cyclopenta[d]pyrimidine
47. 4-(4-Ethoxycarbonylanilino)-6,7-dihydro-7-hydroxy-5H-cyclopenta[d]pyrimidine
48. 4-(4-Ethoxycarbonylanilino)-6,7-dihydro-5-hydroxy-5H-cyclopenta[d]pyrimidine
49. 6,7-Dihydro-7-hydroxy-4-(N-methylanilino)-5H-cyclopenta[d]pyrimidine
50. 6,7-Dihydro-5-hydroxy-4-(N-methylanilino)-5H-cyclopenta[d]pyrimidine
51. 4-(4-Ethyl-N-methylanilino)-6,7-dihydro-7-hydroxy-5H-cyclopenta[d]pyrimidine
52. 4-(4-Ethyl-N-methylanilino)-6,7-dihydro-5-hydroxy-5H-cyclopenta[d]pyrimidine
53. 4-(4-Chloro-N-methylanilino)-6,7-dihydro-7-hydroxy-5H-cyclopenta[d]pyrimidine
54. 4-(4-Chloro-N-methylanilino)-6,7-dihydro-5-hydroxy-5H-cyclopenta[d]pyrimidine
55. 4-(4-Cyano-N-methylanilino)-6,7-dihydro-7-hydroxy-5H-cyclopenta[d]pyrimidine
56. 4-(4-Cyano-N-methylanilino)-6,7-dihydro-5-hydroxy-5H-cyclopenta[d]pyrimidine
57. 7-Acetoxy-4-(4-cyanoanilino)-6,7-dihydro-5H-cyclopenta[d]pyrimidine
58. 5-Acetoxy-4-(4-cyanoanilino)-6,7-dihydro-5H-cyclopenta[d]pyrimidine
59. 4-(4-Cyanoanilino)-6,7-dihydro-7-propionyloxy-5H-cyclopenta[d]pyrimidine
60. 4-(4-Cyanoanilino)-6,7-dihydro-5-propionyloxy-5H-cyclopenta[d]pyrimidine
61. 7-Chloroacetoxy-4-(4-cyanoanilino)-6,7-dihydro-5H-cyclopenta[d]pyrimidine
62. 5-Chloroacetoxy-4-(4-cyanoanilino)-6,7-dihydro-5H-cyclopenta[d]pyrimidine
63. 4-(4-Cyanoanilino)-6,7-dihydro-7-methoxyacetoxy-5H-cyclopenta[d]pyrimidine
64. 4-(4-Cyanoanilino)-6,7-dihydro-5-methoxyacetoxy-5H-cyclopenta[d]pyrimidine
65. 4-(4-Cyanoanilino)-6,7-dihydro-7-trifluoroacetoxy-5H-cyclopenta[d]pyrimidine
66. 4-(4-Cyanoanilino)-6,7-dihydro-5-trifluoroacetoxy-5H-cyclopenta[d]pyrimidine
67. 4-(4-Cyanoanilino)-7-dimethylaminoacetoxy-6,7-dihydro-5H-cyclopenta[d]pyrimidine
68. 4-(4-Cyanoanilino)-5-dimethylaminoacetoxy-6,7-dihydro-5H-cyclopenta[d]pyrimidine
69. 4-(4-Cyanoanilino)-6,7-dihydro-7-phenylacetoxy-5H-cyclopenta[d]pyrimidine
70. 4-(4-Cyanoanilino)-6,7-dihydro-5-phenylacetoxy-5H-cyclopenta[d]pyrimidine
71. 7-Cinnamoyloxy-4-(4-cyanoanilino)-6,7-dihydro-5H-cyclopenta[d]pyrimidine
72. 5-Cinnamoyloxy-4-(4-cyanoanilino)-6,7-dihydro-5H-cyclopenta[d]pyrimidine
73. 7-Benzoyloxy-4-(4-cyanoanilino)-6,7-dihydro-5H-cyclopenta[d]pyrimidine
74. 5-Benzoyloxy-4-(4-cyanoanilino)-6,7-dihydro-5H-cyclopenta[d]pyrimidine
75. 4-(4-Cyanoanilino)-7-(3,4-dimethoxybenzoyloxy)-6,7-dihydro-5H-cyclopenta[d]pyrimidine
76. 4-(4-Cyanoanilino)-5-(3,4-dimethoxybenzoyloxy)-6,7-dihydro-5H-cyclopenta[d]pyrimidine
77. 4-(4-Cyanoanilino)-6,7-dihydro-7-methoxy-5H-cyclopenta*d*]*pyrimidine*
78. 4-(4-Cyanoanilino)-6,7-dihydro-5-methoxy-5H-cyclopenta[d]pyrimidine
79. 4-(4-Cyanoanilino)-7-ethoxy-6,7-dihydro-5H-cyclopenta[d]pyrimidine
80. 4-(4-Cyanoanilino)-5-ethoxy-6,7-dihydro-5H-cyclopenta[d]pyrimidine
81. 4-(4-Cyanoanilino)-6,7-dihydro-7-isopropoxy-5H-cyclopenta[d]pyrimidine
82. 4-(4-Cyanoanilino)-6,7-dihydro-5-isopropoxy-5H-cyclopenta[d]pyrimidine
83. 4-(4-Cyanoanilino)-6,7-dihydro-7-trifluoromethoxy-5H-cyclopenta[d]pyrimidine
84. 4-(4-Cyanoanilino)-6,7-dihydro-5-trifluoromethoxy-5H-cyclopenta[d]pyrimidine
85. 4-(4-Cyanoanilino)-7-cyclopropylmethoxy-6,7-dihydro-5Hcyclopenta[d]pyrimidine
86. 4-(4-Cyanoanilino)-5-cyclopropylmethoxy-6,7-dihydro-5H-cyclopenta[d]pyrimidine
87. 4-(4-Cyanoanilino)-6,7-dihydro-7-(2-methoxyethoxy)-5H-cyclopenta[d]pyrimidine
88. 4-(4-Cyanoanilino)-6,7-dihydro-5-(2-methoxyethoxy)-5H-cyclopenta[d]pyrimidine
89. 4-(4-Cyanoanilino)-7-(2-ethoxyethoxy)-6,7-dihydro-5H-cyclopenta[d]pyrimidine
90. 4-(4-Cyanoanilino)-5-(2-ethoxyethoxy)-6,7-dihydro-5H-cyclopenta[d]pyrimidine 91. 4-(4-Cyanoanilino)-7-(2-dimethylaminoethoxy)-6,7-dihydro-5H-cyclopenta[d]pyrimidine
92. 4-(4-Cyanoanilino)-5-(2-dimethylaminoethoxy)-6,7-dihydro-5H-cyclopenta[d]pyrimidine
93. 4-(4-Cyanoanilino)-7-(2-diethylaminoethoxy)-6,7-dihydro-5H-cyclopenta[d]pyrimidine
94. 4-(4-Cyanoanilino)-5-(2-diethylaminoethoxy)-6,7-dihydro-5H-cyclopenta[d]pyrimidine
95. 7-Benzyloxy-4-(4-cyanoanilino)-6,7-dihydro-5H-cyclopenta[d]pyrimidine
96. 5-Benzyloxy-4-(4-cyanoanilino)-6,7-dihydro-5H-cyclopenta[d]pyrimidine
97. 4-(4-Cyanoanilino)-7-(4-fluorobenzyloxy)-6,7-dihydro-5H-cyclopenta[d]pyrimidine
98. 4-(4-Cyanoanilino)-5-(4-fluorobenzyloxy)-6,7-dihydro-5H-cyclopenta[d]pyrimidine
99. 4-(4-Cyanoanilino)-6,7-dihydro-7-phenacyloxy-5H-cyclopenta[d]pyrimidine
100. 4-(4-Cyanoanilino)-6,7-dihydro-5-phenacyloxy-5H-cyclopenta[d]pyrimidine
101. 4-(4-Cyanoanilino)-6,7-dihydro-7-phenoxy-5H-cyclopenta[d]pyrimidine
102. 4-(4-Cyanoanilino)-6,7-dihydro-5-phenoxy-5H-cyclopenta[d]pyrimidine
103. 7-Allyloxy-4-(4-cyanoanilino)-6,7-dihydro-5H-cyclopenta[d]pyrimidine
104. 5-Allyloxy-4-(4-cyanoanilino)-6,7-dihydro-5H-cyclopenta[d]pyrimidine
105. 4-(4-Cyanoanilino)-6,7-dihydro-5,7-dihydroxy-5H-cyclopenta[d]pyrimidine
106. 5,7-Diacetoxy-4-(4-cyanoanilino)-6,7-dihydro-5H-cyclopenta[d]pyrimidine Of the compounds listed above, the most preferred compounds are Compounds No. 3, 21, 31, 32, 57 and 58.

Broadly speaking, compounds of the present invention can be prepared by reacting a compound of formula (II):

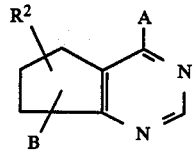

(II)

[in which $R^2$ is as defined above and either:
(i) A represents a halogen atom and B represents any one of the groups defined for $R^1$; or
(ii) B represents a hydrogen atom and A represents a group of formula

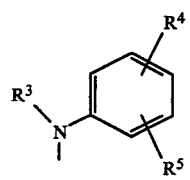

in which $R^3$, $R^4$ and $R^5$ are as defined above]
with either
(i) where A represents a halogen atom, a compound of formula (III):

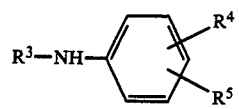

(III)

(in which $R^3$, $R^4$ and $R^5$ are as defined above); or (ii) where B represents a hydrogen atom, with lead tetraacetate to produce a compound of formula (I) where $R^1$ represents an acetoxy group, optionally hydrolysing the acetoxy product to give a compound of formula (I) where $R^1$ represents a hydroxy group, and optionally reacting the hydroxy product with a compound of formula $R^7X$ [in which $R^7$ represents a $C_1$-$C_4$ alkyl group, a substituted $C_1$-$C_4$ alkyl group having at least one substituent selected from the group consisting of substituents (a), a $C_2$-$C_4$ alkenyl group, an aryl group, a $C_2$-$C_5$ aliphatic acyl group, a substituted $C_2$-$C_5$ aliphatic acyl group having at least one substituent selected from the group consisting of substituents (a) or an aromatic acyl group; and X represents a halogen atom].

In more detail, the methods which may be employed to prepare the compounds of the invention are as follows:

Method A

Compounds of the invention in which $R^1$ represents a group AcO— (in which Ac represents an acetyl group), a hydroxy group or a group $R^7O$— (in which $R^7$ is as defined above), that is to say compounds of formulae (V), (VI) and (VII), can be prepared as illustrated in the following reaction scheme:

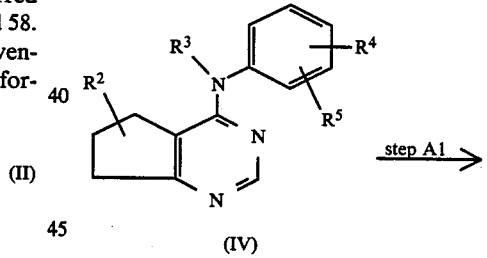

(IV)

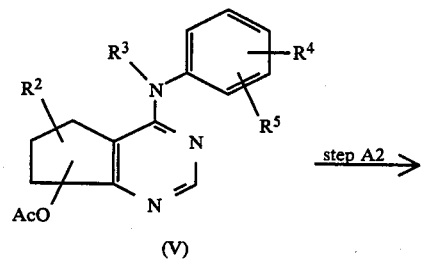

(V)

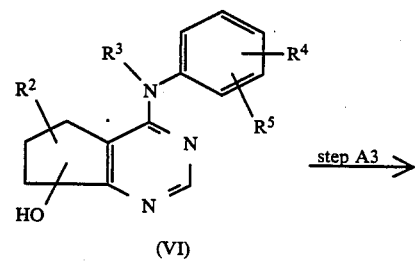

(VI)

-continued

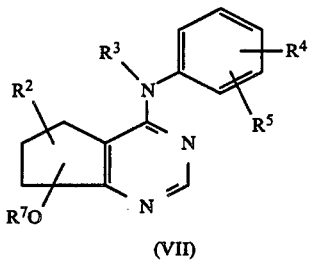

(VII)

In the above formulae, $R^2$, $R^3$, $R^4$, $R^5$, $R^7$ and Ac are as defined above.

The compound of formula (IV) employed as starting material in this process can, when $R^2$ represents a hydrogen atom, be prepared as described in U.S. Pat. No. 4,450,162, the disclosure of which is incorporated herein by reference. The starting material of formula (IV) where $R^2$ represents any group other than a hydrogen atom can be prepared by Method A, starting with a compound in which $R^2$ represents a hydrogen atom, or by the subsequently described Methods B or C.

Step A1

In step A1 of this method, the compound of formula (IV) is reacted with lead tetraacetate to introduce an acetoxy group into the cyclopentene ring.

The amount of lead tetraacetate employed is not particularly critical, although we generally prefer to use an equimolar amount or an excess of the lead tetraacetate, with respect to the compound of formula (IV). Preferably, the molar ratio of lead tetraacetate to compound of formula (IV) is from 1:1 to 10:1.

The reaction is preferably effected in the presence of a solvent, the nature of which is not critical, provided that it has no adverse effect upon the reaction. Examples of suitable solvents include: aromatic hydrocarbons, such as benzene or toluene; organic carboxylic acids, such as acetic acid; lower alcohols, such as methanol or ethanol; ethers, such as diethyl ether or tetrahydrofuran; and organic bases, such as pyridine or triethylamine.

If desired, the reaction may be effected in the presence of a catalyst to accelerate the reaction. Suitable catalysts include Lewis acids, such as boron trifluoride or a boron trifluoride/diethyl ether complex.

The reaction will take place over a wide range of temperatures, but we generally prefer to carry out the reaction at a temperature not less than room temperature, and preferably at a temperature between room temperature and the boiling point of the solvent employed. Preferably, in order that the reaction may be completed speedily, we carry out the reaction at the reflux temperature of the solvent. The time required for the reaction will vary widely, depending upon many factors, notably the reaction temperature and the nature of the reagents, but a period of from 2 hours to 50 hours will normally suffice.

Step A2

In step A2 of this method, the resulting acetoxy compound of formula (V) is, if desired, hydrolized to give the corresponding hydroxy compound (VI). This reaction is carried out in the presence of water and under conditions well-known for hydrolysis of esters.

Although the reaction can be effected using simply water as the solvent, it is preferred to employ additionally an organic solvent, to enhance the solubility of the reagents in the reaction medium. The nature of such organic solvents is not critical, provided that the solvent has no adverse effect upon the reaction. Suitable solvents include, for example: alcohols, such as methanol or ethanol; ketones, such as acetone; ethers, such as dioxane or tetrahydrofuran; nitriles, such as acetonitrile; amides, such as dimethylformamide; or sulfoxides, such as dimethyl sulfoxide.

The reaction is preferably effected in the presence of an acid or a base to catalyse the hydrolysis. The amount of acid or base is not critical and we would normally employ anything from a minor catalytic amount of acid or base to a molar ratio of acid or base to compound of formula (V) of 50:1. Any acid or base commonly employed in such hydrolysis reactions may be used and examples include: mineral acids, such as hydrochloric acid, sulfuric acid, nitric acid or phosphoric acid; organic carboxylic acids, such as formic acid or acetic acid; organic sulfonic acids, such as p-toluenesulfonic acid or methanesulfonic acid; alkali metal hydroxides, such as lithium hydroxide, sodium hydroxide or potassium hydroxide; alkaline earth metal hydroxides, such as calcium hydroxide, barium hydroxide or magnesium hydroxide; alkali metal carbonates or bicarbonates, such as sodium carbonate, potassium carbonate, sodium bicarbonate or potassium bicarbonate; and organic bases, such as pyridine, 4-dimethylaminopyridine, quinoline or triethylamine.

The reaction will take place over a wide range of temperatures, but we generally prefer to carry out the reaction at a temperature from room temperature to about the boiling point of the solvent employed.

Step A3

In step A3 of this reaction, the resulting hydroxy compound is, if desired, converted to the alkoxy, aryloxy or acyloxy compound of formula (VII) by reaction with an acyl halide or alkyl halide or formula $R^7X$ (where $R^7$ is as defined above and X represents a halogen atom, such as chlorine, bromine or iodine).

The nature of the group $R^7$ in the acyl halide or alkyl halide $R^7X$ to be employed will be determined by the nature of the group $R^7$ to be introduced into the compound. $R^7X$ is preferably an acyl halide, alkyl halide, substituted alkyl halide or alkenyl halide. There is no particular limitation on the amount of halide $R^7X$ to be employed, although we generally prefer to employ equimolar amounts of the two reagents or a molar excess of the halide $R^7X$. A preferred molar ratio of halide $R^7X$ to hydroxy compound (VI) is from 1:1 to 5:1.

The reaction is preferably effected in the presence of a solvent, the nature of which is not critical, provided that it has no adverse effect on the reaction. Where the halide $R^7X$ is an acyl halide, the solvent is preferably: an ether, such as diethyl ether, tetrahydrofuran or dioxane; an aromatic hydrocarbon, such as benzene, toluene or xylene; a ketone, such as acetone or methyl isobutyl ketone; a halogenated aliphatic hydrocarbon, such as methylene chloride, 1,2-dichloroethane, chloroform or carbon tetrachloride; an aliphatic hydrocarbon, such as hexane; an ester, such as ethyl acetate; an amide, such as dimethylformamide; or a sulfoxide, such as dimethyl sulfoxide. Where the halide $R^7X$ is an alkyl halide, any one of the above-mentioned solvents may be employed or there may be employed an alcohol, such as methanol or ethanol.

In order to accelerate the reaction, it may be carried out in the presence of an acid-binding agent, the function of which is to remove from the reaction system the hydrohalic acid HX generated by the reaction. Any compound, normally a base, capable of doing this may be used and examples include: alkali metal hydroxides, such as lithium hydroxide, sodium hydroxide or potassium hydroxide; alkaline earth metal hydroxides, such as calcium hydroxide, barium hydroxide or magnesium hydroxide; alkali metal carbonates and bicarbonates, such as sodium carbonate, potassium carbonate, sodium bicarbonate and potassium bicarbonate; and organic amines, such as pyridine, 4-dimethylaminopyridine, quinoline or triethylamine. The amount of acid-binding agent is not particularly critical, but we generally prefer to employ a molar ratio of acid-binding agent to hydroxy compound (VI) of from 1:1 to 5:1.

The reaction will take place over a wide range of temperatures, for example with ice-cooling or at a temperature from room temperature to about the boiling point of the solvent employed.

After completion of these reactions or of any of the reactions, the desired product may be separated from the reaction mixture by conventional separation procedures, and then, if necessary, the resulting product may be purified by such conventional techniques as recrystallization or the various chromatography techniques, especially column chromatography.

Method B

Compounds of formula (I) in which $R^1$ represents a substituted or unsubstituted alkoxy or aryloxy group at the 7-position, that is to say compounds of formula (XIV) can be prepared as illustrated in the following reaction scheme:

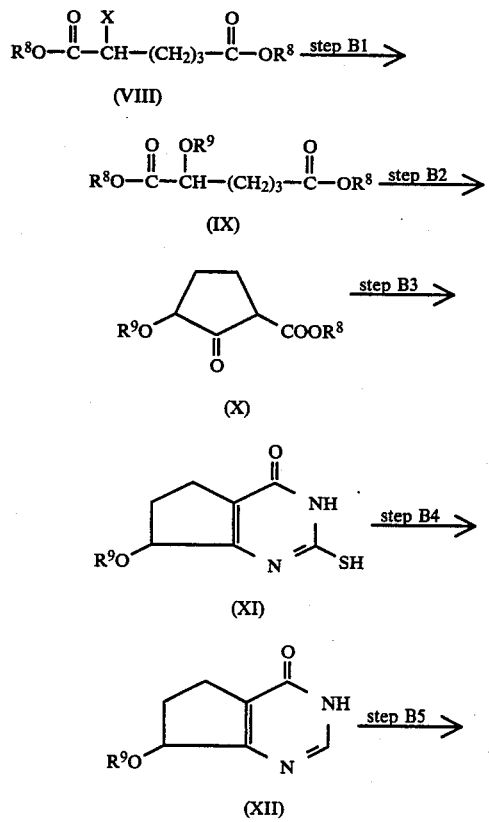

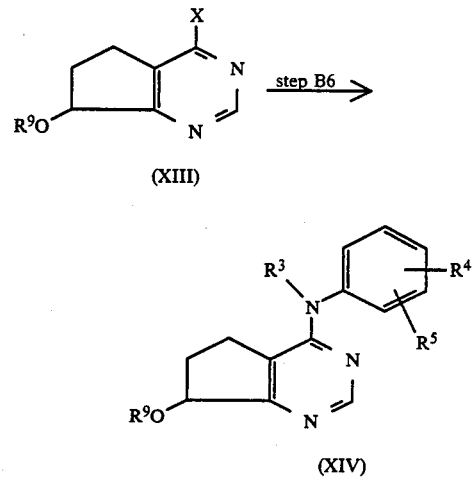

In the above formulae, $R^3$, $R^4$, $R^5$ and X are as defined above. $R^8$ represents an alkyl group. $R^9$ represents a $C_1$–$C_4$ alkyl group, a substituted $C_1$–$C_4$ alkyl group having at least one substituent selected from the group consisting of substituents (a) or an aryl group, i.e. the alkyl and aryl groups corresponding to the alkoxy and aryloxy groups defined for $R^1$.

The nature of the alkyl group represented by $R^8$ is not critical, since this group is eliminated in the course of the reaction. In general, we prefer that it should be a $C_1$–$C_4$ alkyl group, for example a methyl, ethy, propyl, isopropyl, butyl, sec-butyl, isobutyl or t-butyl group, preferably a methyl group.

The compound of formula (VIII), used as the starting material for this method, is disclosed, where X is a bromine atom, in Chem. Ber., 93, 2549 (1960). Corresponding other halo compounds, e.g. the chloro or iodo compounds, may be prepared in a similar way.

Step B1

In step B1 of this method, the alkyl haloadipate of formula (VIII) is reacted with an alkali metal alkoxide or alkali metal aryloxide of formula $MOR^9$ (in which M represents an alkali metal and $R^9$ is as defined above).

The reaction is preferably effected in the presence of a solvent, the nature of which is not critical, provided that it has no adverse effect upon the reaction. Suitable solvents include, for example: alcohols, such as methanol, ethanol or t-butanol; ethers, such as diethyl ether or tetrahydrofuran; and aromatic hydrocarbons, such as benzene, toluene or xylene. We prefer to use an alcohol or an ether and, where an alcohol is used and the compound $MOR^9$ is an alkoxide, it is convenient to use the alcohol corresponding to that alkoxide.

The reaction will take place over a wide range of temperatures and the precise reaction temperature is not particularly critical. However, we generally prefer to carry out the reaction at a temperature within the range from 0° to 50° C. The time required for the reaction will vary, depending upon many factors, notably the reaction temperature and the nature of the reagents; however, a period of from 4 hours to 24 hours will normally suffice.

There is not particular restriction on the nature of the alkali metal M, but sodium, potassium or lithium are normally preferred, sodium being most preferred.

Step B2

In this step, the alkyl alkoxyadipate or aryloxyadipate of formula (IX) is cyclized to give the cyclopentanone derivative of formula (X). This is effected by reacting the alkoxyadipate or aryloxyadipate (IX) with an alkali metal. Preferred alkali metals are lithium, sodium or potassium, more preferrably sodium.

The reaction is preferably effected in the presence of a solvent, the nature of which is not critical, provided that it has no adverse effect upon the reaction. Suitable solvents include, for example: aromatic hydrocarbons, such as benzene, toluene or xylene; aliphatic hydrocarbons, such as hexane or cyclohexane; and ethers, such as diethyl ether or tetrahydrofuran. Of these, the aromatic hydrocarbons are preferred.

The reaction will take place over a wide range of temperatures and the precise reaction temperature is not critical. However, we generally prefer to carry out the reaction at a temperature in the range from 0° to 150° C. The time required for the reaction may vary widely, depending upon many factors, notably the reaction temperature and the nature of the reagents; however, a period of from 2 hours to 16 hours will normally suffice.

Step B3

In this step, a pyrimidin-4-one ring is constructed by reacting the cyclopentanone derivative (X) with thiourea.

The reaction is preferably effected in the presence of a base, more preferably an inorganic base, for example: an alkali metal alkoxide, such as sodium methoxide, potassium methoxide, sodium ethoxide, potassium ethoxide or potassium t-butoxide; an alkali metal hydroxide, such as sodium hydroxide or potassium hydroxide; or an alkali metal carbonate, such as sodium carbonate or potassium carbonate. Of these, the alkali metal hydroxides are preferred.

The reaction is preferably effected in the presence of a solvent, the nature of which is not critical, provided that it has no adverse effect upon the reaction. Suitable solvents include, for example: alcohols, such as methanol, ethanol or propanol; ethers, such as diethyl ether or tetrahydrofuran; water; or a mixture of one or more of the above-mentioned organic solvents with water. Of these, aqueous alcohols are preferred.

The reaction will take place over a wide range of temperatures and the precise reaction temperature chosen is not particularly critical. However, we prefer to carry out the reaction at a temperature in the range from room temperature to 150° C. The time required for the reaction may vary widely, depending upon many factors, notably the reaction temperature and the nature of the reagents; however, a period of from 1 to 6 hours will normally suffice.

Step B4

In this step, the mercapto group at the 2-position of the cyclopenta[d]pyrimidine derivative of formula (XI) is eliminated by reduction.

The reaction is preferably effected by means of a reducing agent, for example Raney nickel and ammonia or Raney nickel and hydrogen. The reaction preferably is carried out in the presence of a solvent, the nature of which is not critical, provided that it has no adverse effect upon the reaction. Suitable solvents include: aqueous ammonia; aqueous alcohols, for example methanol or ethanol; and water, of which aqueous ammonia is preferably employed when Raney nickel/ammonia is used as the reducing agent.

The reaction will take place over a wide range of temperatures and the precise temperature chosen is not particularly critical; however, a temperature between room temperature and 100° C. is generally preferred. The time required for the reaction may vary widely, depending upon many factors, notably the reaction temperature and the nature of the reagents employed; however, a period of from 1 hour to 6 hours will normally suffice.

Step B5

In this step, the cyclopenta[d]pyrimidin-4-one compound of formula (XII) is reacted with a halogenating agent to replace the ketonic oxygen atom by a halogen atom, giving the compound of formula (XIII). Any halogenating agent commonly employed for this type of reaction may be used, provided that it does not interfere with other parts of the molecule. We generally prefer to employ a phosphorus oxyhalide, such as phosphorus oxychloride, phosphorus oxybromide or phosphorus oxyiodide, preferably phosphorus oxychloride.

The reaction will take place without a solvent, or a solvent may be employed. Where a solvent is employed, its nature is not critical, provided that it has no adverse effect upon the reaction. Suitable solvents include halogenated hydrocarbons, preferably halogenated aliphatic hydrocarbons, such as chloroform or carbon tetrachloride.

The reaction will take place over a wide range of temperatures and the precise temperature chosen is not critical. We generally prefer to carry out the reaction at a temperature in the range from room temperature to 150° C. The time required for the reaction will vary widely, depending upon many factors, notably the reaction temperature and the nature of the reagents; however, a period of from 1 minute to 2 hours will normally suffice.

Step B6

In this step, the compound of formula (XIII) is reacted with an aniline derivative of formula (III):

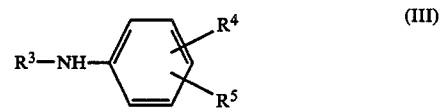

(in which $R^3$, $R^4$ and $R^5$ are as defined above).

This reaction may be carried out in a variety of ways. For example, the halopyrimidine derivative of formula (XIII) may be mixed with at least an equimolar amount of the aniline compound of formula (III) and the mixture heated, with or without a solvent. Alternatively, at least an equimolar amount of the aniline compound of formula (III) may be added to a solution of the halopyrimidine derivative of formula (XIII) and the resulting solution heated. Where a solvent is employed, its nature is not particularly critical, provided that it has no adverse effect upon the reaction; suitable solvents include, for example: alcohols, such as methanol or ethanol; ethers, such as tetrahydrofuran or dioxane; and aromatic hydrocarbons, such as benzene, toluene or xylene.

The reaction temperature is also not critical, but best results are generally achieved by employing a temperature of from 100° C. to 200° C. if no solvent is used or about the reflux temperature of the solvent if a solvent is present.

A catalytic amount of a mineral acid (such as hydrochloric acid or sulfuric acid) can be added to the reaction mixture in order to accelerate the reaction. The time required for the reaction will, of course, depend upon the nature of the reagents and on the presence or absence of the mineral acid, as well as upon the reaction temperature, but the reaction will generally be complete within 1 hour when the reaction is conducted without a solvent and within 24 hours when the reaction is conducted under reflux using a solvent.

Under the reaction conditions described above, the compounds of the invention are generally obtained in the form of a hydrohalic acid salt corresponding to the halogen atom represented by X in the halopyrimidine derivative of formula (XIII), although occasionally the compound of formula (I) in the free form may be obtained, if the aniline compound of formula (III) acts as an acid-binding agent.

Alternatively, in order to obtain the desired compound of formula (I) in the form of the free base, the reaction may be conducted by dissolving the halopyrimidine derivative of formula (XIII) in an organic solvent having a high boiling point (such as toluene, xylene or m-dichlorobenzene), adding to the solution at least one equimolar amount of the aniline compound of formula (III) and at least 1.2 times the molar amount of a base (such as triethylamine) and heating the mixture under reflux at about the boiling temperature of the solvent employed; the reaction will generally be complete within 24 hours.

After completion of the reaction, the compound of the invention may be recovered from the reaction mixture by conventional means, for example by leaving the reaction mixture to cool, collecting the resulting precipitate by filtration and then recrystallizing it from a suitable organic solvent to give the desired compound, generally in the form of the hydrohalic acid salt. Where it is desired to obtain the compound in the form of the free base, the reaction mixture is first made alkaline by the addition of a base (such as an aqueous solution of sodium hydroxide) and it is then extracted with a water-immiscible organic solvent (such as ethyl acetate); the organic phase is then separated and dried and the solvent is distilled off under reduced pressure; finally, the resulting residue is recrystallized from a suitable organic solvent to give the desired product.

Where the compound is obtained in the form of its free base, it can, if necessary, be converted to a pharmaceutically acceptable acid addition salt by conventional salification methods.

Method C

In this method, a cyclopenta[d]pyrimidine derivative of formula (XV) is activated by oxidizing it to the 1-nitrogen oxide, and an acyloxy group is then introduced at the 7-position by reaction with an acid anhydride, after which the resulting compound is reacted with an aniline derivative of formula (III), in a step similar to step B6 described above. These reactions are summarized in the following reaction scheme:

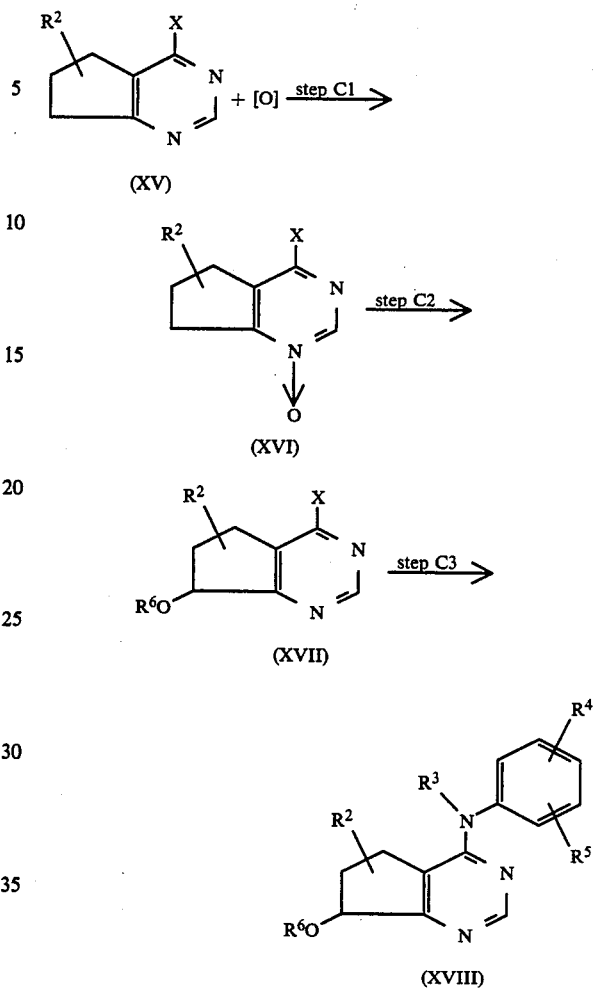

In the above formulae, $R^2$, $R^3$, $R^4$, $R^5$ and X are as defined above. $R^6$ represents a $C_2-C_5$ aliphatic acyl group, a substituted $C_2-C_5$ aliphatic acyl group having at least one substituent selected from the group consisting of substituents (a) or an aromatic acyl group, of which the $C_2-C_5$ aliphatic acyl groups, particularly the acetyl group, are preferred.

Step C1

In this step, the 4-halocyclopenta[d]pyrimidine derivative of formula (XV) is oxidized to give the corresponding N-oxide of formula (XVI).

Any oxidizing agent capable of forming an N-oxide may be used, provided that it does not interfere with other parts of the molecule. Suitable oxidizing agents are: peracids, such as peracetic acid, perbenzoic acid or m-chloroperbenzoic acid; and hydrogen peroxide. The amount of oxidizing agent employed is preferably equimolar or a molar excess with respect to the compound (XV), for example a molar ratio of oxidizing agent to compound (XV) of from 1:1 to 10:1.

The reaction is preferably effected in the presence of a solvent, the nature of which is not critical, provided that it has no adverse effect upon the reaction. Suitable solvents include, for example: halogenated hydrocarbons, preferably halogenated aliphatic hydrocarbons, such as methylene chloride, chloroform or carbon tetrachloride; aliphatic carboxylic acids, such as acetic acid or propionic acid; water; and mixtures of one or more of the above organic solvents with water. The halogenated hydrocarbons are preferred.

The reaction will take place over a wide range of temperatures, for example from −50° C. to +150° C. The time required for the reaction may vary widely, depending upon many factors, notably the reaction temperature and the nature of the reagents; however, a period of from 1 hour to 24 hours will normally suffice.

Step C2

In this step, an acyloxy group $R^6O$ is introduced at the 7-position of the cyclopenta[d]pyrimidine compound by reacting the N-oxide (XVI) with an acid anhydride. The acid anhydride is a compound of formula $(R^6)_2O$, where $R^6$ is as defined above, and the precise compound chosen depends upon the nature of the group $R^6$ which it is desired to introduce into the compound. The acid anhydride is preferably employed in an equimolar amount or a molar excess with respect to the N-oxide of formula (XVI), preferably a molar ratio of acid anhydride to N-oxide (XVI) of from 1:1 to 10:1, except where the acid anhydride is to function as the reaction solvent, in which case its amount is dictated by its solvent function.

The reaction is preferably effected in the presence of a solvent, the nature of which is not critical, provided that it has no adverse effect upon the reaction. Suitable solvents include, for example: aromatic hydrocarbons, such as benzene, toluene or xylene; aliphatic hydrocarbons, such as hexane or heptane; halogenated hydrocarbons, such as methylene chloride, chloroform or carbon tetrachloride; esters, such as ethyl acetate; or an excess of the acid anhydride $(R^6)_2O$.

The reaction will take place over a wide range of temperatures, for example from 0° C. to 150° C. The time required for the reaction may vary widely, depending upon many factors, notably the reaction temperature and the nature of the reagents; however, a period of from 1 hour to 10 hours will normally suffice.

Step C3

This is essentially the same as the reaction described in step B6 of Method B and may be carried out under the same conditions and employing the same reagents.

If desired, in any of the above Methods, the intermediate products may be isolated from the reaction mixture after conclusion of each of the steps mentioned above; alternatively, these reactions may take place without intermediate isolation of these products.

At the end of the reactions, the desired compounds may be separated and recovered from the reaction media by conventional techniques, after which they may be purified by such conventional purification techniques as recrystallization and the various chromatography techniques, particularly column chromatography or preparative thin layer chromatography.

The compounds of the invention have excellent antidepressant activity combined with a low toxicity and relatively few side effects. The compounds may be administered for the treatment of depression by any conventional route and may, if desired, be formulated as compositions suitable to the intended route of administration. For example, they may be administered orally in the form of tablets, capsules, granules, powders or syrups or parenterally by subcutaneous injection, intravenous injection or as a suppository. The pharmaceutical compositions may be prepared by formulating the active ingredient with conventional auxiliary agents, for example excipients, binders, disintegrators, lubricants, flavouring agents, solubilizing agents or suspending agents.

The dose of the compound of the invention will vary, depending upon the condition, age and body weight of the patient, as well as the nature and severity of the disorder and the route of administration. For example, for an adult human patient, the recommended daily dose would normally be from 20 mg to 500 mg, which can be administered as a single dose or in divided doses.

The preparation of compounds of the present invention is illustrated in the following Examples; the preparation of one of the starting materials is illustrated in the subsequent Preparation; and the biological activity of the compounds of the invention is demonstrated by the subsequent Test Examples.

EXAMPLE 1

5-Acetoxy-4-(4-cyanoanilino)-6,7-dihydro-5H-cyclopenta[d]pyrimidine (Compound No. 58) and 7-Acetoxy-4-(4-cyanoanilino)-6,7-dihydro-5H-cyclopenta[d]pyrimidine (Compound No. 57)

14.06 g (0.06 mole) of 4-(4-cyanoanilino)-6,7-dihydro-5H-cyclopenta[d]pyrimidine (prepared following the procedure described in Example 2 of U.S. Pat. No. 4,450,162) were dissolved in 700 ml of acetic acid. 26.58 g (0.06 mole) of lead tetraacetate were added to the resulting solution, and the mixture was heated under reflux for 10 hours. At the end of this time, the insolubles were removed by filtration, and then the solvent was distilled off under reduced pressure. The residue thus obtained was subjected to silica gel column chromatography eluted with ethyl acetate, to give 3.3 g of Compound No. 57 and 3.0 g of Compound No. 58. The two compounds were separately purified by recrystallization from ethyl acetate, to give Compound No. 57 as pale grayish crystals melting at 215°–217° C. and Compound No. 58 as colorless needles melting at 194°–196° C.

EXAMPLE 2

4-(4-Cyanoanilino)-6,7-dihydro-7-hydroxy-5H-cyclopenta[d]pyrimidine (Compound No. 31)

2.9 g (0.01 mole) of Compound No. 57, prepared as described in Example 1, were dissolved in 800 ml of ethanol. 160 ml of an aqueous solution containing 13.8 g (0.1 mole) of potassium carbonate were then added to the resulting solution, and the mixture was stirred overnight at room temperature. At the end of this time, the solvent was removed by distillation under reduced pressure, and the resulting residue was washed with water. The crystals thus obtained were recrystallized from ethanol, giving 1.4 g of the title compound as colorless sandy crystals melting at 260°–262° C. (with decomposition).

EXAMPLE 3

4-(4-Cyanoanilino)-6,7-dihydro-5-hydroxy-5H-cyclopenta[d]pyrimidine (Compound No. 32)

The procedure described in Example 2 was repeated, but using 2.9 g (0.01 mole) of Compound No. 58, prepared as described in Example 1, to give, after recrystallization from ethanol, 1.8 g of the title compound as colorless sandy crystals melting at 232°–234° C. (with decomposition).

EXAMPLE 4

4-(4-Cyanoanilino)-6,7-dihydro-7-methoxy-5H-cyclopenta[d]pyrimidine (Compound No. 77)

(a) Dimethyl α-methoxyadipate 12.2 g of sodium methoxide were added to a solution of 38.0 g of dimethyl α-bromoadipate (prepared as described in the following Preparation) in 100 ml of methanol, and the mixture was stirred overnight at room temperature. After this, methanol was evaporated from the reaction mixture under reduced pressure, and diethyl ether was added to the resulting residue. The solution thus obtained was washed with water and dried over anhydrous sodium sulfate. The diethyl ether was evaporated off under reduced pressure, and the residue was distilled, to give 11.4 g of the title compound, boiling at 74°–79° C./1 mm Hg (133 Pa).

Infrared Absorption Spectrum (liquid film) $v_{max}cm^{-1}$: 1740.

Nuclear Magnetic Resonance Spectrum (CDCl$_3$) δ ppm:
1.56–1.95 (4H, multiplet);
2.24–2.50 (2H, multiplet);
3.38 (3H, singlet);
3.70 (3H, singlet);
3.75 (3H, singlet).

(b) Methyl 3-methoxy-2-oxocyclopentane-1-carboxylate 1.38 g of sodium metal was added to 100 ml of toluene, and the mixture was heated to 60° C. 10.2 g of dimethyl α-methoxyadipate [prepared as described in step (a) above] were then added dropwise to the hot mixture. The mixture was then heated under reflux for 8 hours, after which it was cooled to room temperature and added to a 10% w/v aqueous solution of acetic acid. The organic layer was separated, washed first with a saturated aqueous solution of sodium carbonate and then with water, and then dried over anhydrous sodium sulfate. The solvent was then evaporated off under reduced pressure, and the residue was distilled, to give 4.66 g of the title compound as a pale oil, boiling at 83°–87° C./3 mm Hg (about 400 Pa).

(c) 6,7-Dihydro-2-mercapto-7-methoxy-3H,5H-cyclopenta[d]pyrimidin-4-one 3.44 g of methyl 3-methoxy-2-oxocyclopentane-1-carboxylate [prepared as described in step (b) above] and 1.52 g of thiourea were dissolved in 20 ml of ethanol. A solution of 1.4 g of potassium hydroxide in 10 ml of water was then added to the resulting solution, and the mixture was heated under reflux for 3 hours, after which it was cooled to room temperature. 4 ml of concentrated aqueous hydrochloric acid were added to the mixture, and the crystals which precipitated were collected by filtration, washed with water and dried, to give 1.64 g of the title compound, melting above 250° C.

(d) 6,7-Dihydro-7-methoxy-3H,5H-cyclopenta[d]pyrimidin-4-one 1.58 g of 6,7-dihydro-2-mercapto-7-methoxy-3H,5H-cyclopenta[d]pyrimidin-4-one [prepared as described in step (c) above] and 4 g of Raney nickel were suspended in 15 ml of distilled water, and then 3 ml of concentrated aqueous ammonia were added to the resulting suspension. The mixture was then heated under reflux for 3 hours, after which time the resulting insoluble materials were filtered off from the hot reaction mixture. The filtrate was then evaporated under reduced pressure, to give 1.1 g of the title compound as colorless crystals.

Mass spectrum, m/e: 166 (M+).

(e) 4-Chloro-6,7-dihydro-7-methoxy-5H-cyclopenta[d]pyrimidine 2.5 ml of phosphorus oxychloride were added to 1.0 g of 6,7-dihydro-7-methoxy-3H,5H-cyclopenta[d]pyrimidin-4-one [prepared as described in step (d) above], and the mixture was heated under reflux for 5 minutes. The mixture was then cooled to room temperature, 20 ml of chloroform were added, and the mixture was then poured into ice-water. The cold mixture was made alkaline by the addition of concentrated aqueous ammonia, and then the chloroform layer was separated. This chloroform layer was washed with water, dried over anhydrous sodium sulfate and treated with active carbon. The chloroform was then evaporated off under reduced pressure, to give 1.01 g of the title compound as a colorless oil.

Mass spectrum, m/e: 185 (M+), 153, 149.

Nuclear Magnetic Resonance Spectrum (CDCl$_3$) δ ppm:
2.05–2.23 (1H, multiplet);
2.40–2.58 (1H, multiplet);
2.81–2.97 (1H, multiplet);
3.03–3.24 (1H, multiplet);
3.58 (3H, singlet);
4.80 (1H, doublet of doublets, J=5.7 & 8.6 Hz);
8.88 (1H, singlet).

(f) 4-(4-Cyanoanilino)-6,7-dihydro-7-methoxy-5H-cyclopenta[d]pyrimidine (Compound No 77)

0.92 g of 4-chloro-6,7-dihydro-7-methoxy-5H-cyclopenta[d]pyrimidine [prepared as described in step (e) above] and 0.59 g of p-aminobenzonitrile were dissolved in 5 ml of ethanol, and the solution was stirred at 130° C. for 10 minutes. At the end of this time, the mixture was cooled to room temperature, and the resulting solid reaction product was pulverized. 50 ml of a 1N aqueous solution of sodium hydroxide and 200 ml of ethyl acetate were added to the resulting powder, and the ethyl acetate layer was separated, washed with water and dried over anhydrous sodium sulfate. The ethyl acetate was evaporated off under reduced pressure, and the resulting residue was purified by silica gel column chromatography, eluted with ethyl acetate, to give 0.54 g of the title compound as colorless crystals melting at 167°–169° C.

Infrared Absorption Spectrum (KBr) $v_{max}cm^{-1}$: 3320, 2225.

Nuclear Magnetic Resonance Spectrum (CDCl$_3$) δ ppm:
1.86–2.25 (1H, multiplet);
2.30–2.65 (1H, multiplet);
2.80–3.08 (2H, multiplet);
3.58 (3H, singlet);
4.74 (1H, doublet of doublets, J=4 & 8 Hz);
7.70 (2H, doublet, J=8 Hz);
8.17 (2H, doublet, J=8 Hz);
8.76 (1H, singlet);
9.17 (1H, singlet).

EXAMPLE 5

7-Acetoxy-4-(4-cyanoanilino)-6,7-dihydro-5H-cyclopenta[d]pyrimidine (Compound No. 57)

(a)
4-Chloro-6,7-dihydro-5H-cyclopenta[d]pyrimidine-1-oxide 77.5 g of 4-chloro-6,7-dihydro-5H-cyclopenta[d]pyrimidine were dissolved in 2 liters of chloroform, and then a solution of 259 g of m-chloroperbenzoic acid in 0.1 liter of chloroform was added dropwise. The mixture was stirred overnight, whilst cooling with water, and then a solution of 375 g of sodium thiosulfate in 1.5 liters of water and a solution of 191 g of sodium carbonate in 0.7 liters of water were added successively dropwise, whilst ice-cooling. The chloroform layer was separated, and the aqueous layer was extracted with chloroform. The separated chloroform layer and extracts were combined and dried over anhydrous sodium sulfate. The chloroform was evaporated off under reduced pressure, and the resulting residue was purified by silica gel column chromatography, using ethyl acetate as the eluent, to give 43.9 g of the title compound as colorless crystals melting at 85°-87° C. (with decomposition).

(b)
7-Acetoxy-4-chloro-6,7-dihydro-5H-cyclopenta[d]pyrimidine

A solution of 40 g of 4-chloro-6,7-dihydro-5H-cyclopenta[d]pyrmidine-1-oxide [prepared as described in step (a) above] in 1 liter of acetic anhydride was added dropwise, whilst heating at 50° C., to 1.5 liters of acetic anhydride. After the addition was complete, the solution was stirred at 110° C. for 2 hours. At the end of this time, the mixture was cooled to room temperature, and the solvent was evaporated off under reduced pressure. 400 ml of a mixture of toluene and hexane were added to the resulting residue, the mixture was stirred, and the solvent was separated by decantation; these operations were repeated a further 2 times. The decanted solvents were combined and then evaporated under reduced pressure. The resulting residue was purified by silica gel column chromatography, using chloroform as the eluent, to give 39.3 g of the title compound as a colorless oil.

Mass spectrum, m/e: 170 (M-42), 152, 43.

(c)
7-Acetoxy-4-(4-cyanoanilino)-6,7-dihydro-5H-cyclopenta[d]pyrimidine (Compound No. 57)

39.3 g of 7-acetoxy-4-chloro-6,7-dihydro-5H-cyclopenta[d]pyrimidine [prepared as described in step (b) above] and 24 g of p-aminobenzonitrile were dissolved in 180 ml of ethanol, and the solution was heated under reflux for 1.5 hours. At the end of this time, the solvent was evaporated off under reduced pressure, and the resulting residue was washed with a 1:1 by volume mixture of ethanol and toluene, to give 30 g of the title compound as pale grayish crystals, melting at 215°-217° C.

Mass spectrum, m/e: 294 (M+), 251, 234.

PREPARATION

Dimethyl α-bromoadipate 64 g of methyl hydrogen adipate were added dropwise to 120 ml of thionyl chloride at room temperature, and the solution was heated under reflux for 2 hours. At the end of this time, whilst the solution was still under reflux, 67.2 g of the bromine were added dropwise. The mixture was heated under reflux for a further 5 hours, after which it was allowed to stand overnight at room temperature. The mixture was then added to 400 ml of methanol, and the resulting solution was stirred for 3 hours at room temperature. The solvent was then evaporated off under reduced pressure, and the residue was poured into water and extracted with diethyl ether. The extract was washed with water and dried over anhydrous sodium sulfate. The solvent was evaporated off under reduced pressure, and the residue was distilled, to give 88.1 g of the title compound, boiling at 92°-98° C./2 mm Hg (267 Pa).

Infrared Absorption Spectrum (liquid film) $\nu_{max}$ cm$^{-1}$: 1740.

Nuclear Magnetic Resonance Spectrum (CDCl$_3$) δ ppm:
1.62-1.93 (2H, multiplet);
1.96-2.20 (2H, multiplet);
2.37 (2H, triplet, J=8 Hz);
3.69 (3H, singlet);
3.80 (3H, singlet);
4.24 (1H, triplet, J=8 Hz).

TEST EXAMPLE 1

Test for Anti-reserpine Activity

The test animals used were male mice of the ddy strain, each weighing 23-25 g. Each compound was tested on a group of five such mice. Each test compound was employed in the form of a solution or suspension in a physiological saline solution containing 0.3% w/v carboxymethylcellulose. The test employed was a partial modification of the method of Rubin et al. [J. Pharmacol. Exptl. Therap., 120, 125 (1957)].

2 mg/kg of reserpine were injected subcutaneously into each mouse and, immediately after the injection, the solution or suspension of the test compound was given orally in a dose of 5 mg/kg, 10 mg/kg or 25 mg/kg, as shown in the following Table. The animals were observed 90 minutes, 120 minutes and 180 minutes after administration to evaluate the inhibition of ptosis. At each observation, each mouse was assigned from 0 to 3 points corresponding to the degree of ptosis, as follows:

0 points: eyes completely open;
1 point: eyes about one third closed;
2 points: eyes about two thirds closed;
3 points: eyes completely closed.

For each mouse, the number of points from all three observations were added together, and the percentage inhibition of reserpine-induced ptosis (Ri) was calculated from the following formula:

$$Ri = [(P_o - P_t)/P_o] \times 100$$

in which:

$P_o$ = total number of points from three observations of an animal to which reserpine alone was administered; and $P_t$ = total number of points from three observations of an animal to which reserpine and the test compound were administered.

The results are shown in the following Table.

TEST EXAMPLE 2

Acute Toxicity Test

The test animals used were male rats of the F-344 strain, each weighing from 150 to 170 g. One group of animals was fed normally, whilst another group was starved for 24 hours before administration of the test compound. To each animal was administered orally a single dose of the test compound in the amount shown in the following Table; the animals were then placed under observation for 7 days after administration. The results are reported in Table as "Mortality", where the numerator indicates the number of deaths in the observation period and the denominator indicates the number of animals tested with the particular test compound at the particular dose.

TABLE

| Cpd No | Ri % (dose) | Mortality (dose) fed | starved |
|---|---|---|---|
| 31 | 50 (5 mg) | 0/5 (800 mg) | 0/5 (1500 mg) |
|  | 71.4 (10 mg) |  |  |
|  | 85.7 (25 mg) |  |  |
| A | 85.0 (25 mg) | 1/5 (200 mg) | 3/5 (200 mg) |

The compound of the invention is identified by the number heretofore assigned in the foregoing list, whilst Compound A is 4-(4-cyanoanilino)-6,7-dihydro-5H-cyclopenta[d]pyrimidine (Compound No. 14 from U.S. Pat. No. 4,450,162).

TEST EXAMPLE 3

Toxicity to the Liver

The inhibition of monoamine oxidase in the rat liver by Compound No. 31 and Compound A were assessed, and it was estimated, on the basis of this assessment that the toxicity to the liver of the compound of the invention was about half that of the prior art compound.

We claim:

1. A compound of formula (I):

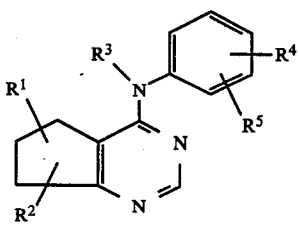

wherein:

$R^1$ represents a hydroxy group, a $C_1$-$C_4$ alkoxy group, a substituted $C_1$-$C_4$ alkoxy group having at least one substituent selected from the group consisting of substituents (a), a $C_2$-$C_4$ alkenyloxy group, an aryloxy group, a $C_2$-$C_5$ aliphatic acyloxy group, a substituted $C_2$-$C_5$ aliphatic acyloxy group having at least one substituent selected from the group consisting of substituents (a) or an aromatic acyloxy group;

$R^2$ represents a hydrogen atom, a hydroxy group, a $C_1$-$C_4$ alkoxy group, a substituted $C_1$-$C_4$ alkoxy group having at least one substituent selected from the group consisting of substituents (a), a $C_2$-$C_4$ alkenyloxy group, an aryloxy group, a $C_2$-$C_5$ aliphatic acyloxy group, a substituted $C_2$-$C_5$ aliphatic acyloxy group having at least one substituent selected from the group consisting of substituents (a) or an aromatic acyloxy group;

$R^3$ represents a hydrogen atom or a $C_1$-$C_4$ alkyl group;

$R^4$ and $R^5$ are independently selected from the group consisting of hydrogen atoms, $C_1$-$C_4$ alkyl groups, $C_1$-$C_4$ alkoxy groups, hydroxy groups, $C_2$-$C_5$ aliphatic acyloxy groups, aryloxy groups, $C_1$-$C_4$ haloalkyl groups, halogen atoms, nitro groups, $C_1$-$C_4$ alkanesulfonyl groups, arylsulfonyl groups, cyano groups and carboxy groups; or $R^4$ and $R^5$ together represent a $C_1$ or $C_2$ alkylenedioxy group;

said substituents (a) are selected from the group consisting of $C_1$-$C_4$ alkoxy groups, $C_3$-$C_7$ cycloalkyl groups, halogen atoms, dialkylamino groups where both alkyl parts are $C_1$-$C_4$, aromatic acyl groups and aryl groups;

said aryl groups and the aryl parts of said aromatic acyl, aromatic acyloxy, aryloxy and arylsulfonyl groups being $C_6$-$C_{10}$ carbocyclic aromatic hydrocarbon groups which are unsubstituted or have at least one substituent selected from the group consisting of substituents (b); and said substituents (b) are selected from the group consisting of $C_1$-$C_4$ alkyl groups, $C_1$-$C_4$ alkoxy groups, $C_3$-$C_7$ cycloalkyl groups, halogen atoms and dialkylamino groups here both alkyl parts are $C_1$-$C_4$;

and pharmaceutically acceptable salts and esters thereof.

2. A compound as claimed in claim 1, wherein $R^2$ represents a hydrogen atom and the group represented by $R^1$ is at the 5- or 7-position.

3. A compound as claimed in claim 1, wherein $R^2$ represents any of said groups other than the hydrogen atom and is at the 5- or 7-position, and $R^1$ is at the 7- or 5-position.

4. A compound as claimed in claim 1, in which:

$R^1$ represents a hydroxy group, a $C_1$-$C_4$ alkoxy group or a $C_2$-$C_5$ aliphatic acyloxy group at the 5- or 7-position;

$R^2$ represents a hydrogen atom, or a hydroxy, $C_1$-$C_4$ alkoxy or $C_2$-$C_5$ aliphatic acyloxy group at the 7-5-position;

$R^3$ represents a hydrogen atom;

$R^4$ represents a hydrogen atom, a $C_1$-$C_4$ alkyl group, a $C_1$-$C_4$ haloalkyl group, a halogen atom, a nitro group, a $C_1$-$C_4$ alkanesulfonyl group, a cyano group, a carboxy group or a $C_2$-$C_5$ alkoxycarbonyl group; and $R^5$ represents a hydrogen or halogen atom.

5. A compound as claimed in claim 1, in which:

$R^1$ represents a hydroxy group or an acetoxy group at the 5- or 7-position;

$R^2$ and $R^3$ represent hydrogen atoms;

$R^4$ represents a $C_1$-$C_4$ alkyl group, a trifluoromethyl group, a halogen atom or a cyano group at the 4-position; and $R^5$ represents a hydrogen atom or a halogen atom at the 3-position.

6. A compound as claimed in claim 1, in which:

$R^1$ represents a hydroxy group or an acetoxy group at the 5- or 7-position;

$R^2$, $R^3$ and $R^5$ all represent hydrogen atoms; and $R^4$ represents an ethyl group, a chlorine atom or a cyano group at the 4-position.

7. A pharmaceutical composition comprising an effective amount of an antidepressant compound in admixture with a pharmaceutically acceptable carrier or diluent, wherein the antidepressant compound is selected from the group consisting of compounds of formula (I):

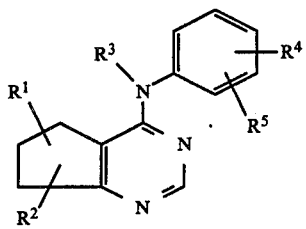

(I)

wherein:
$R^1$ represents a hydroxy group, a $C_1$–$C_4$ alkoxy group, a substituted $C_1$–$C_4$ alkoxy group having at least one substituent selected from the group consisting of substituents (a), a $C_2$–$C_4$ alkenyloxy group, an aryloxy group, a $C_2$–$C_5$ aliphatic acyloxy group, a substituted $C_2$–$C_5$ aliphatic acyloxy group having at least one substituent selected from the group consisting of substituents (a) or an aromatic acyloxy group;

$R^2$ represents a hydrogen atom, a hydroxy group, a $C_1$–$C_4$ alkoxy group, a substituted $C_1$–$C_4$ alkoxy group having at least one substituent selected from the group consisting of substituents (a), a $C_2$–$C_4$ alkenyloxy group, an aryloxy group, a $C_2$–$C_5$ aliphatic acyloxy group, a substituted $C_2$–$C_5$ aliphatic acyloxy group having at least one substituent selected from the group consisting of substituents (a) or an aromatic acyloxy group;

$R^3$ represents a hydrogen atom or a $C_1$–$C_4$ alkyl group;

$R^4$ and $R^5$ are independently selected from the group consisting of hydrogen atoms, $C_1$–$C_4$ alkyl groups, $C_1$–$C_4$ alkoxy groups, hydroxy groups, $C_2$–$C_5$ aliphatic acyloxy groups, aryloxy groups, $C_1$–$C_4$ haloalkyl groups, halogen atoms, nitro groups, $C_1$–$C_4$ alkanesulfonyl groups, arylsulfonyl groups, cyano groups and carboxy groups; or $R^4$ and $R^5$ together represent a $C_1$ or $C_2$ alkylenedioxy group;

said substituents (a) are selected from the group consisting of $C_1$–$C_4$ alkoxy groups, $C_3$–$C_7$ cycloalkyl groups, halogen atoms, dialkylamino groups where both alkyl parts are $C_1$–$C_4$, aromatic acyl groups and aryl groups;

said aryl groups and the aryl parts of said aromatic acyl, aromatic acyloxy, aryloxy and arylsulfonyl groups being $C_6$–$C_{10}$ carbocyclic aromatic hydrocarbon groups which are unsubstituted or have at least one substituent selected from the group consisting of substituents (b); and said substituents (b) are selected from the group consisting of $C_1$–$C_4$ alkyl groups, $C_1$–$C_4$ alkoxy groups. $C_3$–$C_7$ cycloalkyl groups, halogen atoms and dialkylamino groups where both alkyl parts are $C_1$–$C_4$;

and pharmaceutically acceptable salts and esters thereof.

8. A composition as claimed in claim 7, wherein $R^2$ represents a hydrogen atom and the group represented by $R^1$ is at the 5- or 7-position.

9. A composition as claimed in claim 7, wherein $R^2$ represents any of said groups other than the hydrogen atom and is at the 5- or 7-position, and $R^1$ is at the 7- or 5-position.

10. A composition as claimed in claim 7, in which:
$R^1$ represents a hydroxy group, a $C_1$–$C_4$ alkoxy group or a $C_2$–$C_5$ aliphatic acyloxy group at the 5- or 7-position;
$R^2$ represents a hydrogen atom, or a hydroxy, $C_1$–$C_4$ alkoxy or $C_2$–$C_5$ aliphatic acyloxy group at the 7- or 5-position;
$R^3$ represents a hydrogen atom;
$R^4$ represents a hydrogen atom, a $C_1$–$C_4$ alkyl group, a $C_1$–$C_4$ haloalkyl group, a halogen atom, a nitro group, a $C_1$–$C_4$ alkanesulfonyl group, a cyano group, a carboxy group or a $C_2$–$C_5$ alkoxycarbonyl group; and
$R^5$ represents a hydrogen or halogen atom.

11. A composition as claimed in claim 7, in which:
$R^1$ represents a hydroxy group or an acetoxy group at the 5- or 7-position;
$R^2$ and $R^3$ both represent hydrogen atoms;
$R^4$ represents a $C_1$–$C_4$ alkyl group, a trifluoromethyl group, a halogen atom or a cyano group at the 4-position; and
$R^5$ represents a hydrogen atom or a halogen atom at the 3-position.

12. A composition as claimed in claim 7, in which:
$R^1$ represents a hydroxy group or an acetoxy group at the 5- or 7-position;
$R^2$, $R^3$ and $R^5$ all represent hydrogen atoms; and
$R^4$ represents an ethyl group, a chlorine atom or a cyano group at the 4-position.

13. A composition as claimed in claim 7, wherein said antidepressant compound is selected from the group consisting of:
4-(4-Ethylanilino)-6,7-dihydro-7-hydroxy-5H-cyclopenta[d]pyrimidine
4-(4-Chloroanilino)-6,7-dihydro-7-hydroxy-5H-cyclopenta[d]pyrimidine
4-(4-Cyanoanilino)-6,7-dihydro-7-hydroxy-5H-cyclopenta[d]pyrimidine
4-(4-Cyanoanilino)-6,7-dihydro-5-hydroxy-5H-cyclopenta[d]pyrimidine
7-Acetoxy-4-(4-cyanoanilino)-6,7-dihydro-5H-cyclopenta[d]pyrimidine
5-Acetoxy-4-(4-cyanoanilino)-6,7-dihydro-5H-cyclopenta[d]pyrimidine
and pharmaceutically acceptable salts thereof.

14. A method of treating depressive conditions in an animal by administering to said animal an antidepressant compound, wherein said antidepressant compound is selected from the group consisting of compounds of formula (I):

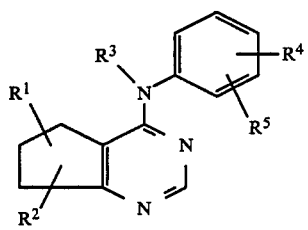

(I)

wherein:
$R^1$ represents a hydroxy group, a $C_1$–$C_4$ alkoxy group, a substituted $C_1$–$C_4$ alkoxy group having at least one substituent selected from the group consisting of substituents (a), a $C_2-C_4$ alkenyloxy group, an aryloxy group, a $C_2-C_5$ aliphatic acyloxy group, a substituted $C_2-C_5$ aliphatic acyloxy group having at least one substituent selected from the group consisting of substituents (a) or an aromatic acyloxy group;

$R^2$ represents a hydrogen atom, a hydroxy group, a $C_1-C_4$ alkoxy group, a substituted $C_1-C_4$ alkoxy group having at least one substituent selected from the group consisting of substituents (a), a $C_2-C_4$ alkenyloxy group, an aryloxy group, a $C_2-C_5$ aliphatic acyloxy group, a substituted $C_2-C_5$ aliphatic acyloxy group having at least one substituent selected from the group consisting of substituents (a) or an aromatic acyloxy group;

$R^3$ represents a hydrogen atom or a $C_1-C_4$ alkyl group;

$R^4$ and $R^5$ are independently selected from the group consisting of hydrogen atoms, $C_1-C_4$ alkyl groups, $C_1-C_4$ alkoxy groups, hydroxy groups, $C_2-C_5$ aliphatic acyloxy groups, aryloxy groups, $C_1-C_4$ haloalkyl groups, halogen atoms, nitro groups, $C_1-C_4$ alkanesulfonyl groups, arylsulfonyl groups, cyano groups and carboxy groups; or $R^4$ and $R^5$ together represent a $C_1$ or $C_2$ alkylenedioxy group;

said substituents (a) are selected from the group consisting of $C_1-C_4$ alkoxy groups, $C_3-C_7$ cycloalkyl groups, halogen atoms, dialkylamino groups where both alkyl parts are $C_1-C_4$, aromatic acyl groups and aryl groups;

said aryl groups and the aryl parts of said aromatic acyl, aromatic acyloxy, aryloxy and arylsulfonyl groups being $C_6-C_{10}$ carbocyclic aromatic hydrocarbon groups which are unsubstituted or have at least one substituent selected from the group consisting of substituents (b); and said substituents (b) are selected from the group consisting of $C_1-C_4$ alkyl groups, $C_1-C_4$ alkoxy groups, $C_3-C_7$ cycloalkyl groups, halogen atoms and dialkylamino groups where both alkyl parts are $C_1-C_4$; and pharmaceutically acceptable salts and esters thereof.

15. A method as claimed in claim 14, wherein $R^2$ represents a hydrogen atom and the group represented by $R^1$ is at the 5- or 7-position.

16. A method as claimed in claim 14, wherein $R^2$ represents any of said groups other than the hydrogen atom and is at the 5- or 7-position, and $R^1$ is at the 7- or 5-position.

17. A method as claimed in claim 14, in which:
$R^1$ represents a hydroxy group, a $C_1-C_4$ alkoxy group or a $C_2-C_5$ aliphatic acyloxy group at the 5- or 7-position;
$R^2$ represents a hydrogen atom, or a hydroxy, $C_1-C_4$ alkoxy or $C_2-C_5$ aliphatic acyloxy group at the 7- or 5-position;
$R^3$ represents a hydrogen atom;
$R^4$ represents a hydrogen atom, a $C_1-C_4$ alkyl group, a $C_1-C_4$ haloalkyl group, a halogen atom, a nitro group, a $C_1-C_4$ alkanesulfonyl group, a cyano group, a carboxy group or a $C_2-C_{hd 5}$ alkoxycarbonyl group; and
$R^5$ represents a hydrogen or halogen atom.

18. A method as claimed in claim 14, in which:
$R^1$ represents a hydroxy group or an acetoxy group at the 5- or 7-position;
$R^2$ and $R^3$ both represent hydrogen atoms;
$R^4$ represents a $C_1-C_4$ alkyl group, a trifluoromethyl group, a halogen atom or a cyano group at the 4-position; and
$R^5$ represents a hydrogen atom or a halogen atom at the 3-position.

19. A method as claimed in claim 14, in which:
$R^1$ represents a hydroxy group or an acetoxy group at the 5- or 7-position;
$R^2$, $R^3$ and $R^6$ all represent hydrogen atoms; and
$R^4$ represents an ethyl group, a chlorine atom or a cyano group at the 4-position.

20. A method as claimed in claim 14, wherein said antidepressant compound is selected from the group consisting of:
4-(4-Ethylanilino)-6,7-dihydro-7-hydroxy-5H-cyclopenta[d]pyrimidine
4-(4-Chloroanilino)-6,7-dihydro-7-hydroxy-5H-cyclopenta[d]pyrimidine
4-(4-Cyanoanilino)-6,7-dihydro-7-hydroxy-5H-cyclopenta[d]pyrimidine
4-(4-Cyanoanilino)-6,7-dihydro-5-hydroxy-5H-cyclopenta[d]pyrimidine
7-Acetoxy-4-(4-cyanoanilino)-6,7-dihydro-5H-cyclopenta[d]pyrimidine
5-Acetoxy-4-(4-cyanoanilino)-6,7-dihydro-5H-cyclopenta[d]pyrimidine
and pharmaceutically acceptable salts thereof.

21. A method as claimed in claim 14, wherein said animal is human.

22. The compound of claim 1 designated 4-(4-Ethylanilino)-6,7-dihydro-7-hydroxy-5H-cyclopenta[d]pyrimidine and pharmaceutically acceptable salts thereof.

23. The compound of claim 1 designated 4-(4-Chloroanilino)-6,7-dihydro-7-hydroxy-5H-cyclopenta[d]pyrimidine and pharmaceutically acceptable salts thereof.

24. The compound of claim 1 designated 4-(4-Cyanoanilino)-6,7-dihydro-7-hydroxy-5H-cyclopenta[d]pyrimidine and pharmaceutically acceptable salts thereof.

25. The compound of claim 1 designated 4-(4-Cyanoanilino)-6,7-dihydro-5-hydroxy-5H-cyclopenta[d]pyrimidine and pharmaceutically acceptable salts thereof.

26. The compound of claim 1 designated 7-Acetoxy-4-(4-cyanoanilino)-6,7-dihydro-5H-cyclopenta[d]pyrimidine and pharmaceutically acceptable salts thereof.

27. The compound of claim 1 designated 5-Acetoxy-4-(4-cyanoanilino)-6,7-dihydro-5H-cyclopenta[d]pyrimidine and pharmaceutically acceptable salts thereof.

* * * * *

UNITED STATES PATENT AND TRADEMARK OFFICE
CERTIFICATE OF CORRECTION

PATENT NO. : 4,749,704
DATED : June 7, 1988
INVENTOR(S) : IWATA et al It is certified that error appears in the above-identified patent and that said Letters Patent is hereby corrected as shown below:

Column 6, line 32, change "cycloopenta" to read --cyclopenta--.

Column 8, line 42, change "cyclopentad]" to read --cyclopenta[d]--.

Column 26, line 29 (Claim 1), change "here" to --where--.

Column 30, line 16 (Claim 19), change "and $R^6$" to --and $R^5$--.

Signed and Sealed this

Fifth Day of May, 1992

*Attest:*

DOUGLAS B. COMER

*Attesting Officer*  *Acting Commissioner of Patents and Trademarks*